US009867627B2

(12) United States Patent
Fritzinger et al.

(10) Patent No.: US 9,867,627 B2
(45) Date of Patent: Jan. 16, 2018

(54) QUICK-CONNECT DRILL GUIDE

(71) Applicant: Biomet Manufacturing, LLC, Warsaw, IN (US)

(72) Inventors: Daniel D. Fritzinger, Warsaw, IN (US); Jamie D. Winchester, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 150 days.

(21) Appl. No.: 14/950,105

(22) Filed: Nov. 24, 2015

(65) Prior Publication Data
US 2016/0074051 A1    Mar. 17, 2016

Related U.S. Application Data

(63) Continuation of application No. 13/297,297, filed on Nov. 16, 2011, now Pat. No. 9,198,677.

(51) Int. Cl.
*A61B 17/80* (2006.01)
*A61B 17/17* (2006.01)

(52) U.S. Cl.
CPC .......... *A61B 17/1728* (2013.01); *A61B 17/80* (2013.01)

(58) Field of Classification Search
CPC .................................................. A61B 17/1728
See application file for complete search history.

(56) References Cited

U.S. PATENT DOCUMENTS

| 9,198,677 | B2 | 12/2015 | Fritzinger et al. |
| 2006/0100637 | A1 | 5/2006 | Rathbun et al. |
| 2008/0132900 | A1 | 6/2008 | Prien et al. |
| 2008/0140130 | A1* | 6/2008 | Chan .................. A61B 17/1728 606/280 |
| 2010/0305570 | A1 | 12/2010 | Sarangapani et al. |
| 2013/0123856 | A1 | 5/2013 | Fritzinger et al. |

OTHER PUBLICATIONS

"U.S. Appl. No. 13/297,297, Corrected Notice of Allowance dated Aug. 12, 2015", 5 pgs.
"U.S. Appl. No. 13/297,297, Examiner Interview Summary dated Sep. 18, 2014", 3 pgs.
(Continued)

*Primary Examiner* — Samuel Hanna
(74) *Attorney, Agent, or Firm* — Schwegman Lundberg & Woessner, P.A.

(57) ABSTRACT

A drill guide for use with a bone plate is provided in accordance with various aspects of the present teachings. The drill guide can include a body and a quick-connect coupling arrangement. The body can have a proximal end, a distal end and can define a guide passage therebetween. The distal end can have a bone plate engaging portion. The quick-connect coupling arrangement can be associated with the bone plate engaging portion, and can include first and second lobes projecting radially outward from an outer surface of the bone plate engaging portion. The bone plate engaging portion and the first and second lobes can be operable to be slidably received in a bone screw hole in the bone plate so as to removably couple the drill guide to the bone plate in a predetermined orientation relative to the bone screw hole.

15 Claims, 9 Drawing Sheets

(56) References Cited

OTHER PUBLICATIONS

"U.S. Appl. No. 13/297,297, Final Office Action dated May 16, 2014", 12 pgs.
"U.S. Appl. No. 13/297,297, Non Final Office Action dated Jan. 28, 2014", 10 pgs.
"U.S. Appl. No. 13/297,297, Non Final Office Action dated Mar. 12, 2015", 10 pgs.
"U.S. Appl. No. 13/297,297, Notice of Allowance dated Jul. 31, 2015", 9 pgs.
"U.S. Appl. No. 13/297,297, Response filed Jul. 13, 2015 to Non Final Office Action dated Mar. 12, 2015", 12 pgs.
"U.S. Appl. No. 13/297,297, Restriction Requirement dated Nov. 27, 2013", 9 pgs.

* cited by examiner

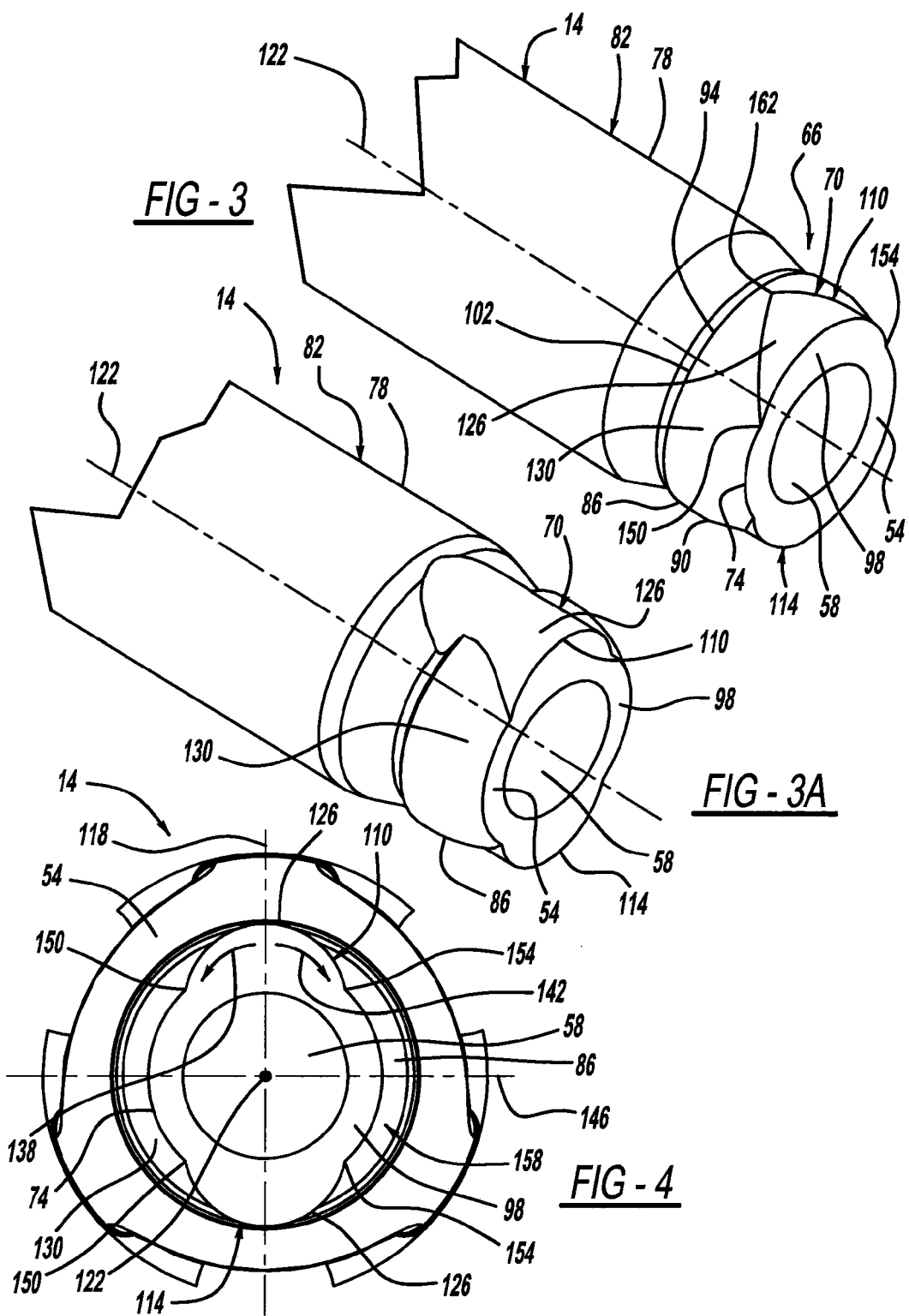

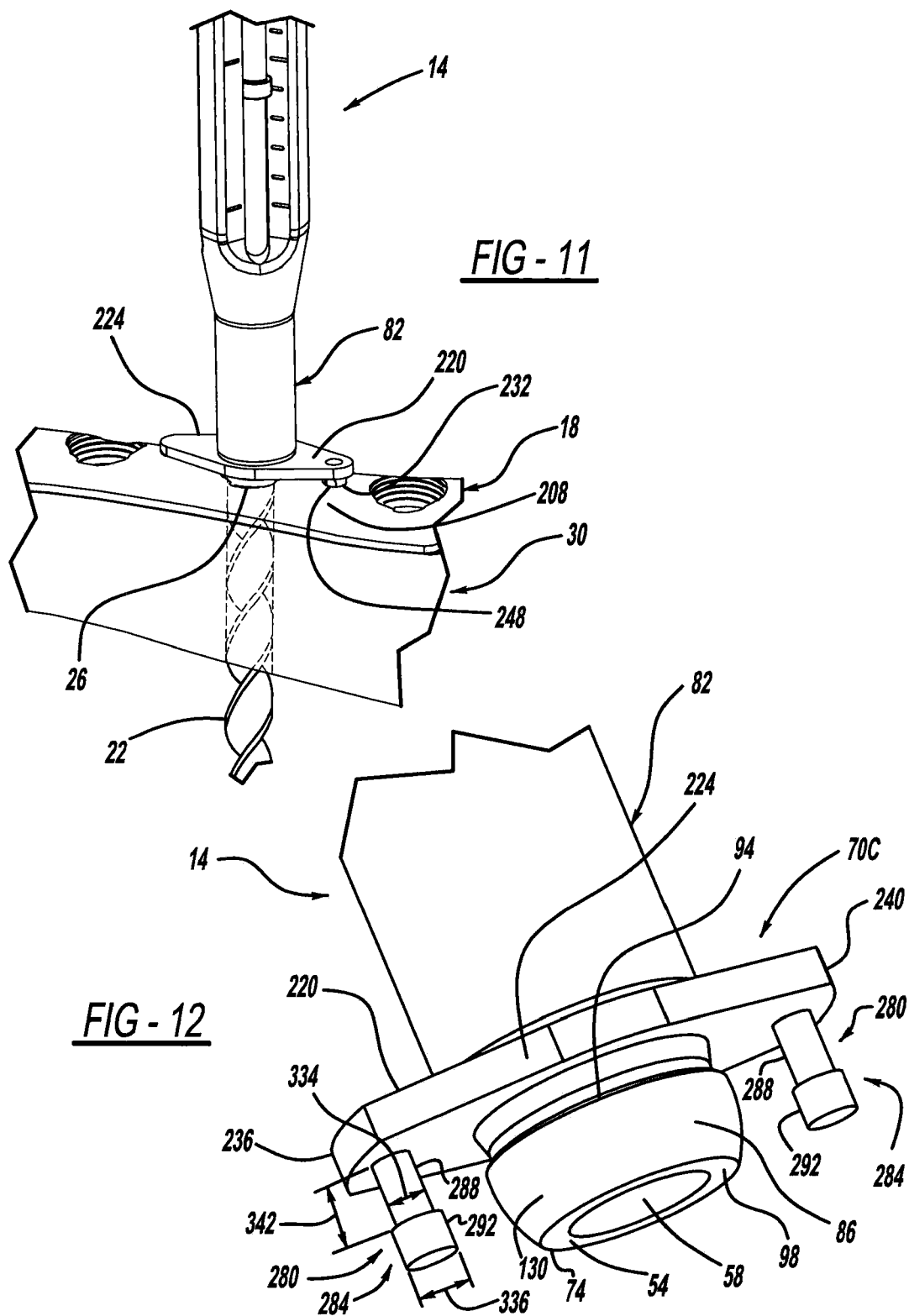

QUICK-CONNECT DRILL GUIDE

RELATED APPLICATIONS

This application is a continuation of U.S. patent application Ser. No. 13/297,297, filed Nov. 16, 2011, issued on Dec. 1, 2015 as U.S. Pat. No. 9,198,677.

FIELD

The present disclosure relates generally to a quick-connect drill guide and, more particularly, to a quick-connect drill guide for use with a bone plate.

BACKGROUND

This section provides background information related to the present disclosure which is not necessarily prior art.

Surgical fixation or bone plates are used in various forms by surgeons to align, stabilize and/or compress bony structures. For example, bone plates are often used in conjunction with fasteners, such as bone screws, to stabilize and compress a bone fracture to promote healing. The bone fasteners can be inserted through holes in the bone plate to affix the bone plate to the corresponding bone. Drill guides can be used to allow for proper placement of the bone screws. The drill guides can assist in drilling a hole in the bone in alignment with its associated bone plate hole. In this regard, various drill guides can be threadably engaged with a desired bone plate hole to ensure proper alignment with the bone plate hole. As bone plating systems often have several bone plate holes and associated bone screws, it can be time consuming and tedious for a surgeon to threadably engage and disengage such a drill guide with each bone plate hole.

Thus, while current bone plating systems and associated drill guides work for their intended purpose, there remains a need for improvement in the relevant art.

SUMMARY

This section provides a general summary of the disclosure, and is not a comprehensive disclosure of its full scope or all of its features.

In one aspect, a drill guide for use with a bone plate is provided in accordance with various aspects of the present teachings. The drill guide can include a body and a quick-connect coupling arrangement. The body can have a proximal end and a distal end and can define a guide passage therebetween. The distal end can have a bone plate engaging portion. The quick-connect coupling arrangement can be associated with the bone plate engaging portion, and can include first and second lobes projecting radially outward from an outer surface of the bone plate engaging portion. The bone plate engaging portion and the first and second lobes can be adapted to be slidably received in a bone screw hole in the bone plate so as to removably couple the drill guide to the bone plate in a predetermined orientation relative to the bone screw hole.

In another aspect, a drill guide assembly is provided in accordance with the teachings of the present disclosure. The drill guide assembly can include a drill guide and a bone plate. The drill guide can include a body and a quick-connect coupling arrangement. The body can have a proximal end and a distal end and can define a guide passage therebetween. The distal end can have a bone plate engaging portion. The quick-connect coupling arrangement can be associated with the bone plate engaging portion, and can include first and second lobes projecting radially outward from an outer surface of the bone plate engaging portion so as to form a generally oblong shaped distal end of the body. The bone plate can have a bone screw hole adapted to receive a bone screw. The bone screw hole can have a generally circular perimeter sidewall with opposed first and second cut-outs formed in the sidewall that are sized and shaped to correspond to the first and second lobes. The bone plate engaging portion and the first and second lobes can be configured to be slidably received in the bone screw hole so as to removably couple the drill guide to the bone plate in a predetermined orientation relative to the bone screw hole.

In yet another aspect, a drill guide assembly is provided in accordance with the teachings of the present disclosure. The drill guide assembly can include a drill guide and a bone plate. The drill guide can include a body and a quick-connect coupling arrangement. The body can have a proximal end and a distal end and can define a guide passage therebetween. The distal end can have a bone plate engaging portion. The quick-connect coupling arrangement can be associated with the body proximate the bone plate engaging portion, and can include a flange extending from the body proximate the distal end and first and second T-shaped pins extending axially from the flange toward the distal end. The bone plate can have a bone screw hole and first and second arcuate slots. The bone screw hole can be adapted to receive a bone screw and can have a perimeter sidewall. The first and second arcuate slots can be formed in the bone plate in spaced relation to the bone screw hole. Each slot can include an enlarged portion at a first end and a retaining portion extending from the enlarged portion to a second opposite end. The bone plate engaging portion can be configured to be received in the bone screw hole and the first and second T-shaped pins can be configured to be received through the respective enlarged portions of the first and second slots in a first position relative to the bone plate. The drill guide can be rotated about an axis of the hole to rotate the first and second pins from the first position to a second position in the retaining portions of the first and second slots to removably couple the drill guide to the bone plate.

Further areas of applicability will become apparent from the description provided herein. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only of selected embodiments and not all possible limitations, and are not intended to limit the scope of the present disclosure.

FIG. 3 is an enlarged perspective view of a distal end of the drill guide of FIG. 1 in accordance with the teachings of the present disclosure;

FIG. 3A is a perspective view of a distal end of an exemplary drill guide in accordance with the teachings of the present disclosure;

FIG. 4 is a distal end view of the drill guide of FIG. 1 in accordance with the teachings of the present disclosure;

FIG. 11 is a view of the drill guide of FIG. 9 releasably connected to the exemplary bone plate of FIG. 10 in accordance with the teachings of the present disclosure;

FIG. 12 is a partial perspective view of a distal end of an exemplary drill guide in accordance with the teachings of the present disclosure;

DETAILED DESCRIPTION

Figure 1:
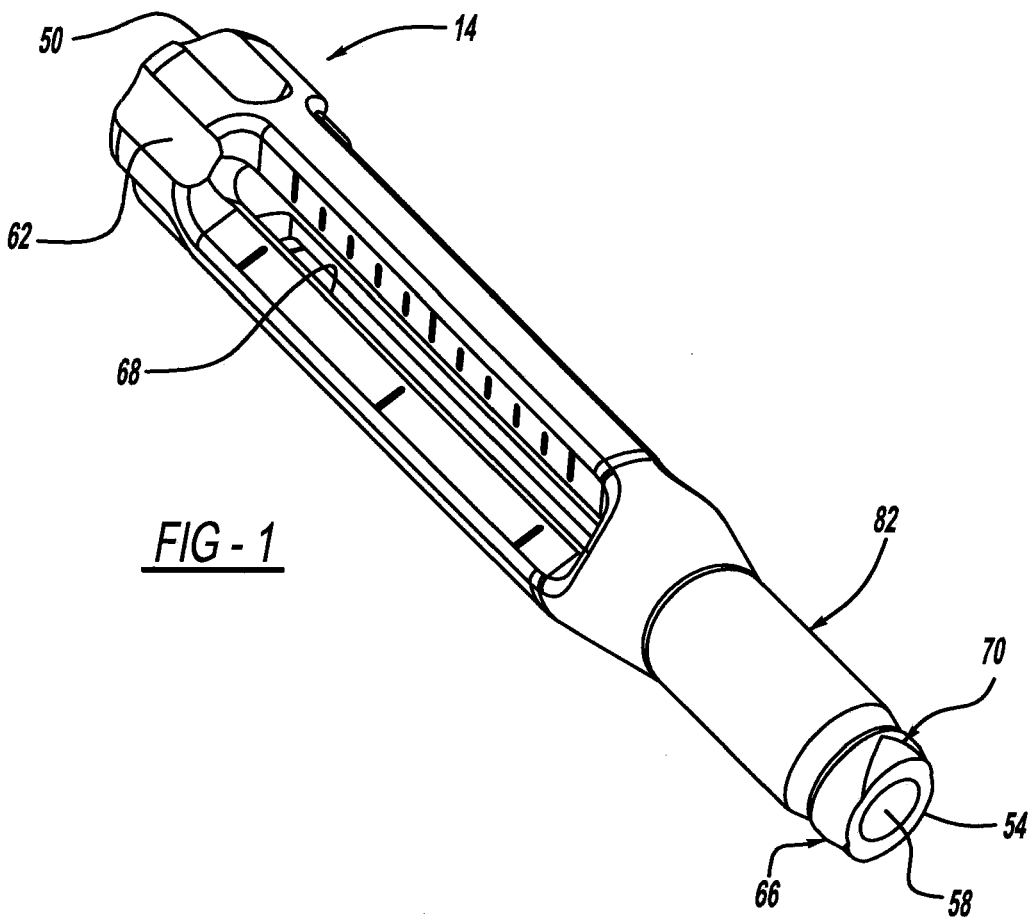
FIG. 1 is a perspective view of an exemplary quick-connect drill guide in accordance with the teachings of the present disclosure.

The following description is merely exemplary in nature and is not intended to limit the present disclosure, its application, or uses. It should be understood that throughout the drawings, corresponding reference numerals indicate like or corresponding parts and features with the various elements in each view being drawn to scale. Although the following description is related generally to a quick-connect drill guide that can be used with an associated bone plate, it should be appreciated that the quick-connect drill guides and associated releasable coupling arrangements discussed herein can also be used to guide other tools or members relative to various structures.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

Figure 2:
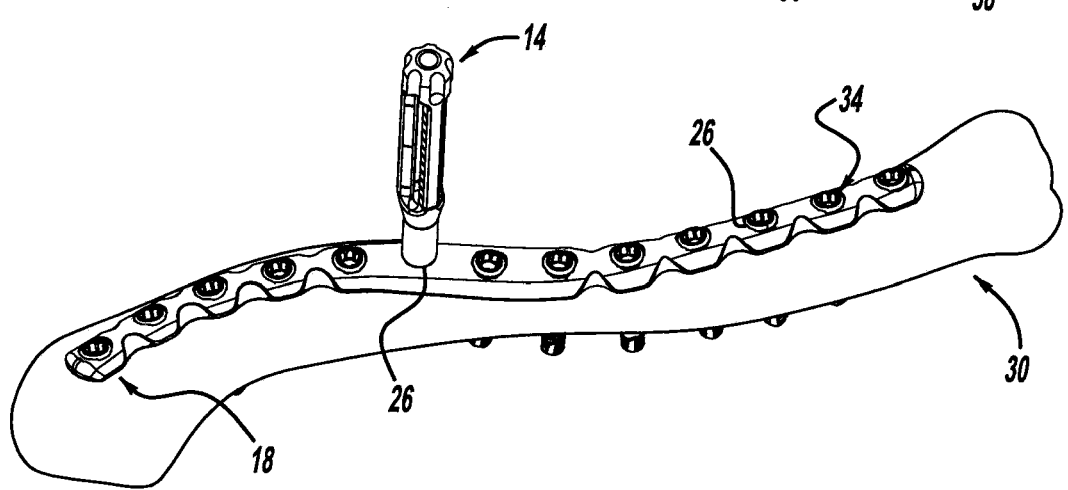
FIGS. 2 and 2A are perspective views of the drill guide of FIG. 1 operatively associated with an exemplary bone plate in accordance with the teachings of the present disclosure.
Figure 2A:
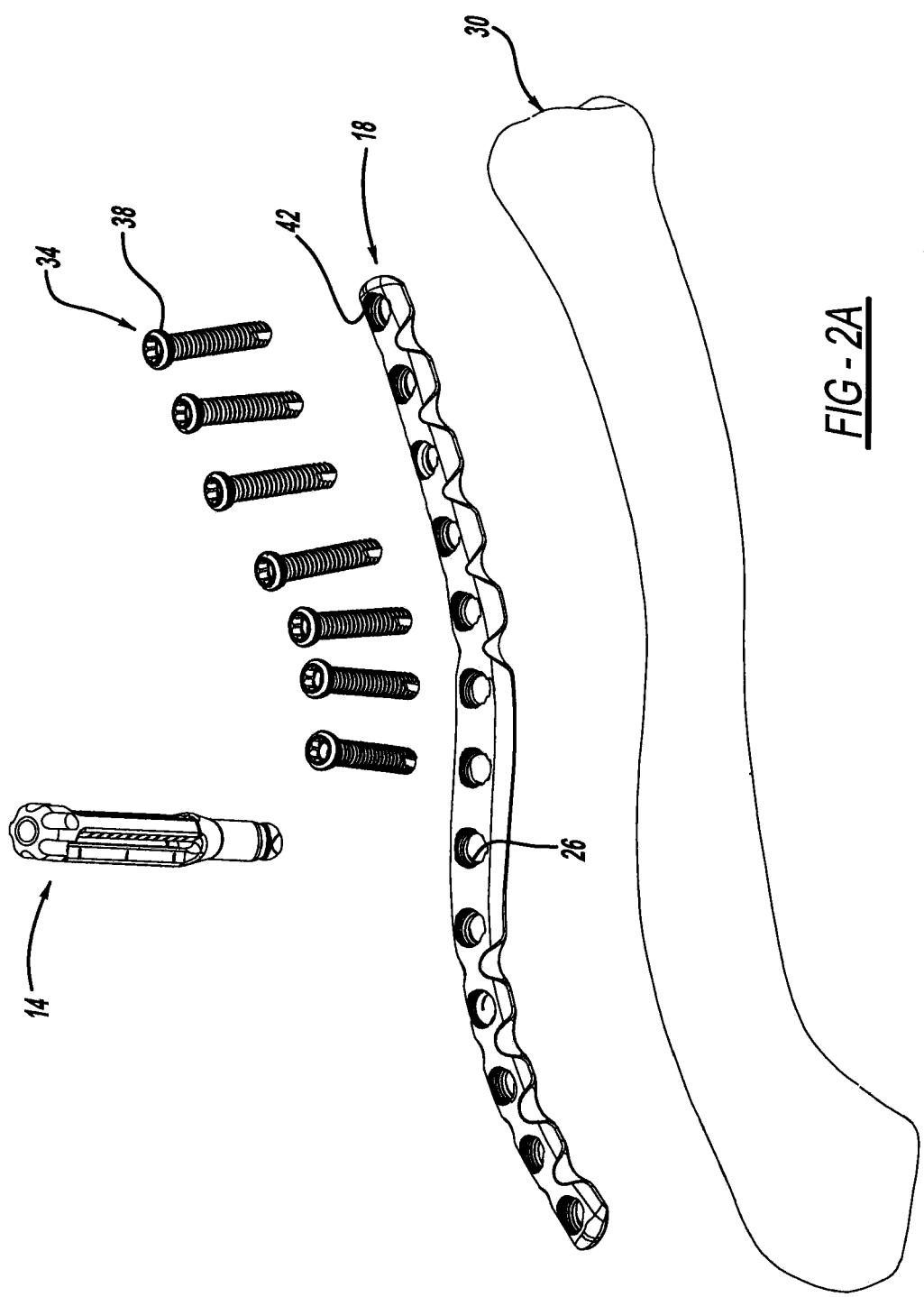

With initial reference to FIGS. 1-3A, an exemplary drill guide 14 is shown and can be operatively associated with an exemplary bone plate 18. Drill guide 14 can be used to facilitate aligning a longitudinal axis 20 of a drill 22 (FIG. 10) with an axis 24 (FIGS. 5 and 6) of an associated bone plate hole 26 in plate 18 for drilling an appropriate hole in exemplary bone 30. Bone screws, such as the locking bone screws 34 shown in FIG. 2A, can be used to secure bone plate 18 to bone 30. In one exemplary aspect, bone screws 34 can include an externally threaded head 38 configured for threadable engagement with internal threads 42 of one of the bone plate holes 26, as also shown for example in FIG. 2A. It should be appreciated that while bone plate 18 and various exemplary aspects thereof will continue to be referenced throughout the description, the drill guide 14 and the exemplary quick-connect coupling aspects that will be discussed herein can be used with various other bone plates as may be desired by a surgeon and/or other user.

Drill guide 14 can include a proximal end 50, a distal end 54 and an internal guide passage 58 extending therebetween. Proximal end 50 can include a handle or user engageable portion 62 and at least one elongated through slot 68 configured to provide visual access to drill 22 when positioned through guide passage 58. The distal end 54 can include a bone plate engaging portion 66 and a quick-connect arrangement 70 configured to facilitate efficiently removably coupling drill guide 14 to associate bone plate 18, as will be discussed in greater detail below.

In one exemplary aspect shown in FIG. 3, the bone plate engaging portion 66 can have a first outer diameter 102 smaller than an outer diameter 78 of an adjacent body portion 82 of drill guide 14 extending from the bone plate engaging portion 66 at least partially toward the proximal end 50. The bone plate engaging portion 66 can also include a rounded or tapered end 86 to facilitate ease of entry and removal into and from the bone plate hole 26. In the exemplary configuration illustrated in FIGS. 1-3A, the tapered end 86 can include an arcuate sidewall 90 extending in an axial direction of drill guide 14 generally from a first end 94 of the bone plate engaging portion 66 having the first outer diameter 102 to a second end 98 having a second outer diameter 74 smaller than the first outer diameter 102. In this exemplary configuration, the second end 98 can form the distal end 54.

With continuing reference to FIGS. 3-6, one exemplary quick-connect arrangement 70 of drill guide 14 will now be discussed. In this exemplary aspect, quick-connect arrangement 70 can be provided on the bone plate engaging portion 66 and can be configured to facilitate removably coupling drill guide 14 to bone plate hole 26 in an efficient manner. In this regard, and as will be discussed in greater detail below, quick-connect arrangement 70 can provide for slidably advancing drill guide 14 into engagement with bone plate hole 26 such that the bone plate engaging portion 66 having quick-connect arrangement 70 is slidably received in bone plate hole 26 along the axis 24 thereof.

The exemplary quick-connect arrangement 70 shown in FIGS. 3-6 can include first and second lobes 110, 114 formed or provided on the bone engaging portion 66. The lobes 110, 114 can be diametrically opposed from each other and can extend in a longitudinal direction of the drill guide 14 from the second end 98 of bone engaging portion 66 to at least the first end 94, as shown for example in FIG. 3. In this exemplary configuration, the lobes 110, 114 can each form a protrusion along a first axis 118 that bisects each lobe and is perpendicular to a longitudinal axis 122 of drill guide 14, as shown for example in FIGS. 3 to 4. In other words, each lobe 110, 114 can extend radially outward along a cross-sectional direction of drill guide 14 taken perpendicular to the longitudinal axis 122.

Each lobe 110, 114 can also have an arcuate outer surface shape 126 extending or projecting outward along first axis 118 from an outer surface 130 of tapered end 86. In one exemplary configuration, the arcuate outer shape 126 at the second end 98 can extend circumferentially in first and second directions 138, 142 from first axis 118 up to one-half the circumferential distance or 45 degrees toward a second axis 146 that is perpendicular to the first axis 118 and the longitudinal axis 122. In this exemplary configuration, the arcuate outer shape 126 at the second end 98 can extend slightly less than 45 degrees in the first and second directions 138, 142 to first and second ends 150, 154, as shown for example in FIGS. 3 and 4. In one exemplary configuration, the arcuate outer shape 126 of each lobe 110, 114 can be hemispherical. The arcuate outer shape 126 of each lobe can form a non-circular or generally oblong/oval shape 158 at distal end 54 in a cross-sectional direction, as shown for example in FIG. 4.

In one exemplary configuration, each lobe 110, 114 can extend between the first and second ends 94, 98 of tapered end 86. In this exemplary configuration, the each lobe 110, 114 can have a first width at the distal end 54 between the first and second ends 150, 154 that narrows to or substantially to a point 162 as each lobe 110, 114 extends in the longitudinal direction from the second end 98 to or substantially to the first end 94 of tapered end 86, as shown in FIG. 3. In this regard, each lobe 110, 114 in this configuration can include a larger width at the second end 98 as compared to the first end 94, as also shown in FIG. 3. In another exemplary configuration shown in FIG. 3A, each lobe 110, 114 can extend from the second end 98 of tapered end 86 to the adjacent body portion 82.

Figure 5:
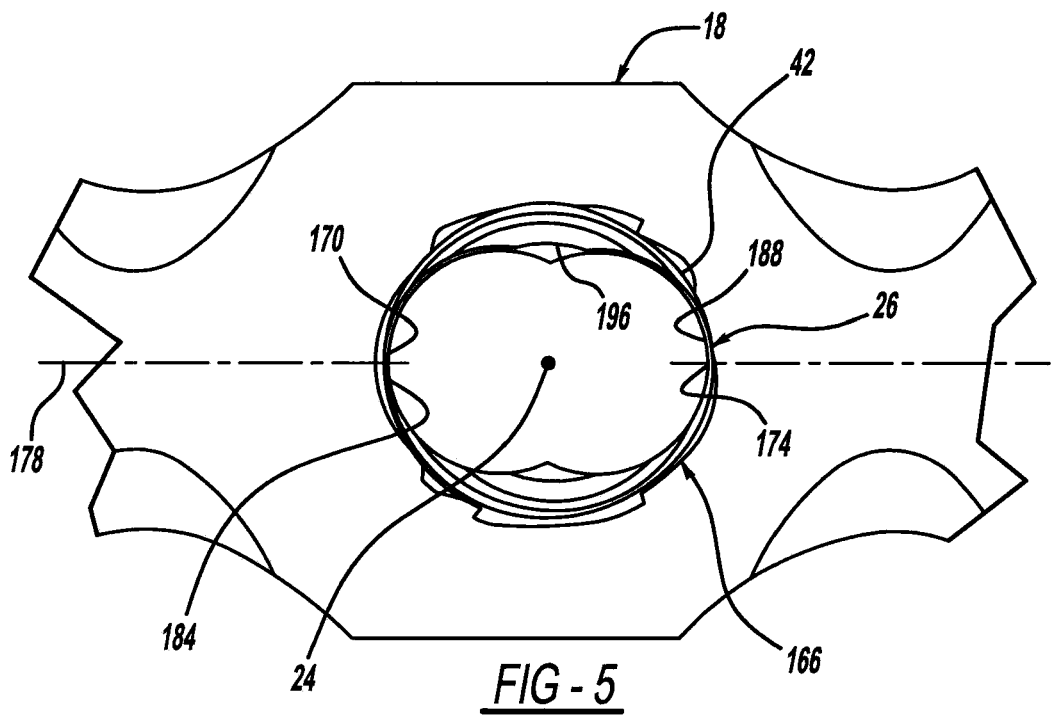
FIG. 5 is a partial top view of one exemplary coupling aspect of the bone plate in accordance with the teachings of the present disclosure.
Figure 6:
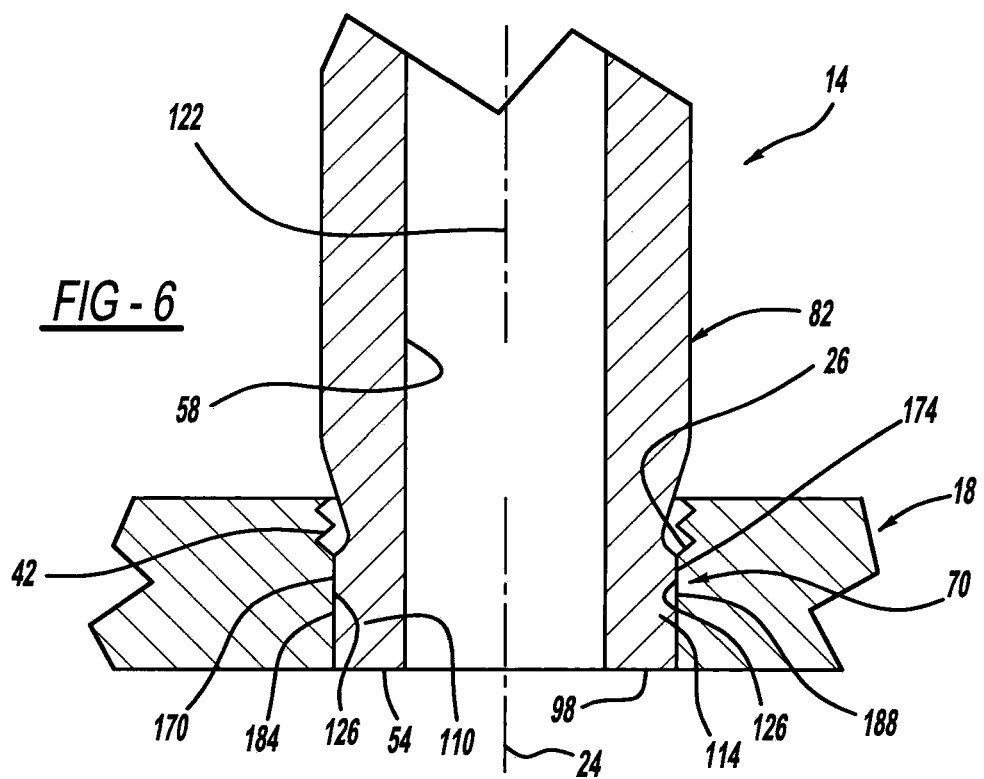
FIG. 6 is a cross-sectional view of the drill guide of FIG. 1 releasably connected to the bone plate of FIG. 5 in accordance with the teachings of the present disclosure.

As briefly discussed above, drill guide 14 can be configured to be removably coupled to bone plate 18. In particular, and with additional reference to FIGS. 5 and 6, each lobe 110, 114 of quick-connect arrangement 70 can be slidably received in bone plate hole 26 so as to removably connect or couple drill guide 14 thereto. In this regard, each bone plate hole that is configured to cooperate with drill guide 14 can include a portion sized and shaped so as to be complementary to the lobes 110, 114 of quick-connect arrangement 70. For example, plate hole 26 can include an overall oblong or non-circular shape 166 generally complementary to the oblong or non-circular shape 158 of quick-connect arrangement 70, as shown for example in FIGS. 5 and 6. The non-circular shape 166 of bone plate hole 26 can include first and second arcuate recesses or cut-outs 170, 174 sized and shaped complementary to lobes 110, 114. In the exemplary configuration shown in FIGS. 5 and 6, the cut-outs 170, 174 can extend in opposite directions generally along a longitudinal axis 178 of bone plate 18. The arcuate outer shape 126 of each lobe 110, 114 can engage a respective sidewall 184, 188 of cut-outs 170, 174, as shown in FIG. 6.

In operation, drill guide 14 can be efficiently coupled to and removed from bone plate holes 26 via quick-coupling arrangement 70. Each lobe 110, 114 of quick-coupling arrangement 70 can be slidably received in a snug or slip-fit manner in the respective cut-outs 170, 174 so as to removably connect or couple drill guide 14 to bone plate 18 in a rotationally fixed manner and in alignment with axis 24 of the bone plate hole 26, as shown for example in FIG. 6 with reference to FIG. 2. In this regard, drill guide 14 can be removably coupled to bone plate 18 in a predetermined orientation. The outer surface 130 of tapered end 86 can also engage at least a portion 196 of bone plate hole 26 extending between cut-outs 170, 174, as generally shown in FIG. 5. The drill 22 or another cutting device can be received in and guided by drill guide 14 to form a hole or bore in bone 30 along the bone plate hole axis 24. Drill guide 14 can then be easily and efficiently slidably removed from hole 26 by the surgeon without having to take additional steps to de-couple guide 14 from bone plate 18, such as unthreading guide 14 therefrom and/or releasing a latching mechanism.

Figure 7:
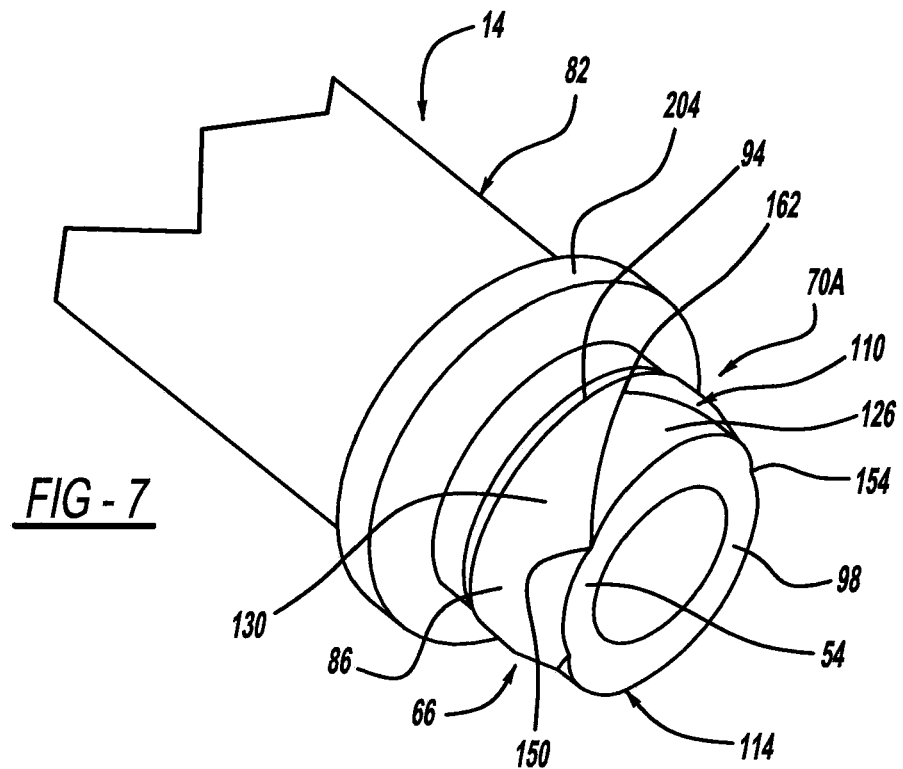
FIG. 7 is a partial perspective view of an exemplary drill guide in accordance with the teachings of the present disclosure.
Figure 8:
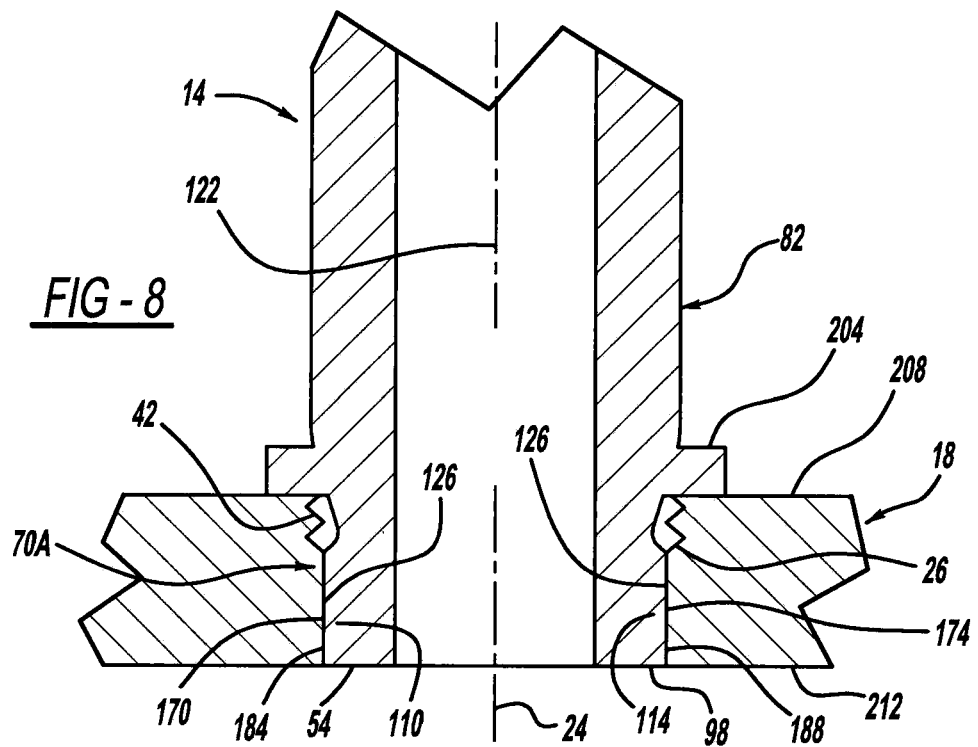
FIG. 8 is a cross-sectional view of the drill guide of FIG. 8 releasably connected to the bone plate of FIG. 5 in accordance with the teachings of the present disclosure.

With additional reference to FIGS. 7 and 8, another exemplary quick-connect arrangement 70A is shown associated with the distal end 54 of drill guide 14. Quick-connect arrangement 70A can be similar to quick-connect arrangement 70 such that like reference numbers refer to like or corresponding features and only differences will be discussed in detail below. Quick-connect arrangement 70A can also include an annular flange 204 positioned proximate the lobes 110, 114, as shown in FIG. 7. Annular flange 204 can extend radially outward from body portion 82 and can be configured to engage a top surface 208 of bone plate 18 adjacent hole 26. In this regard, in the exemplary configuration illustrated, annular flange 204 can be positioned a predetermined distance from distal end 54 so as to provide for the distal end 54 extending into bone plate hole 26 to or substantially to a bone engaging side 212 of bone plate 18, as shown in FIG. 8. It is appreciated, however, that flange 204 can be positioned at other distances from distal end 54, such as closer thereto, to vary the depth at which drill guide 14 is inserted into bone plate hole 26.

In operation, drill guide 14 can be removably connected to bone plate 18 such that lobes 110, 114 engage cut-outs 170, 174 in a similar manner as discussed above. In addition, drill guide 14 can be slidably inserted into bone plate hole 26 until annular flange 204 engages top surface 208 of bone plate 18. Annular flange 204 can provide additional stability for maintaining drill guide 14 in alignment with bone plate hole axis 24, as also generally shown in FIG. 8.

Figures 9, 10:
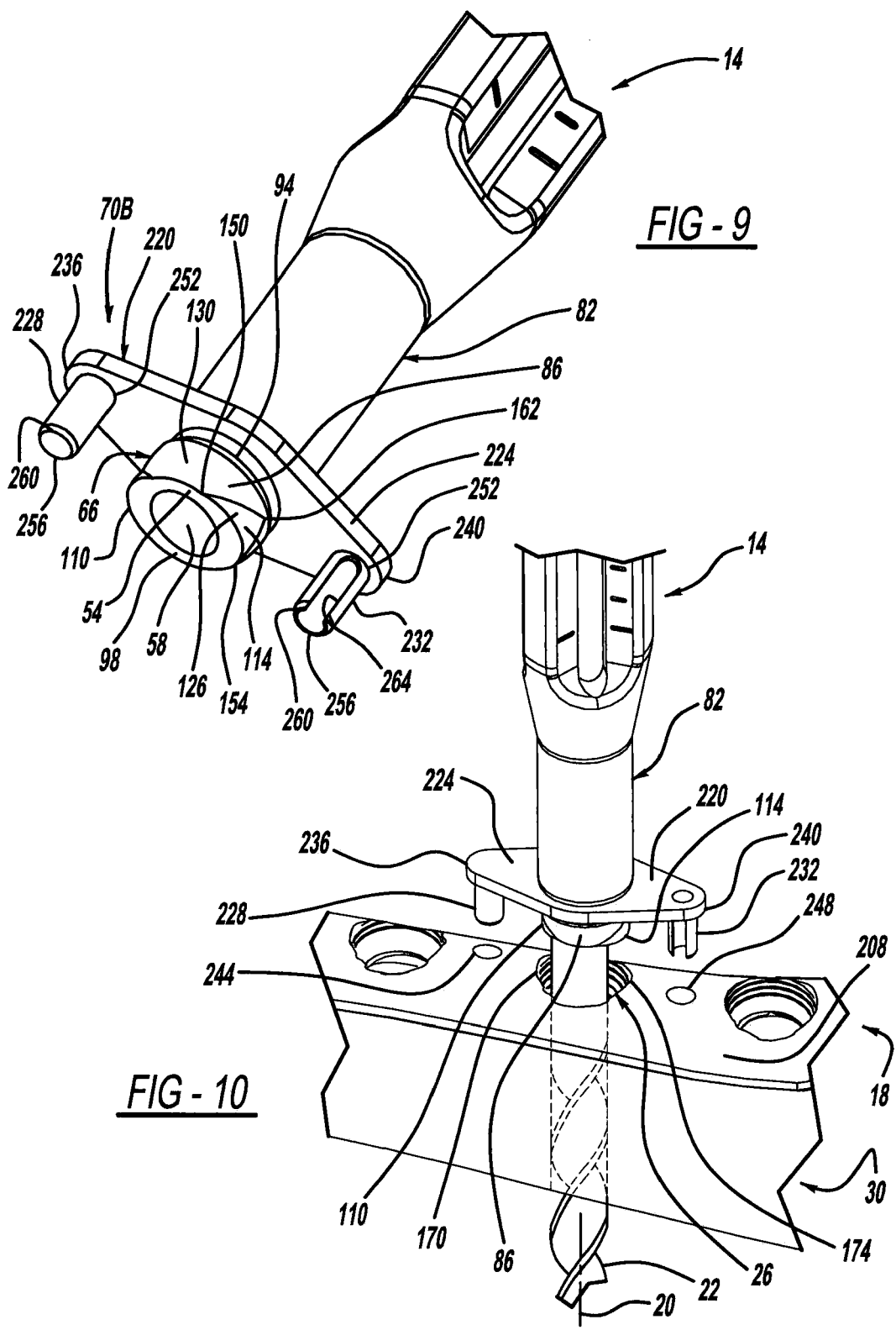
FIG. 9 is a partial perspective view of a distal end of an exemplary drill guide in accordance with the teachings of the present disclosure.
FIG. 10 is a view of the drill guide of FIG. 9 positioned relative to an associated exemplary bone plate in accordance with the teachings of the present disclosure.

With additional reference to FIGS. 9-11, another exemplary quick-connect arrangement 70B is shown associated with the distal end 54 of drill guide 14. Quick-connect arrangement 70B can be similar in certain aspects to quick-connect arrangements 70, 70A such that like reference numbers refer to like or corresponding features and only differences will be discussed in detail below. With initial reference to FIG. 9, quick-connect arrangement 70B can include a flange 220 in place of annular flange 204 of quick-connect arrangement 70A. In one exemplary configuration, flange 220 can include an elongated body 224 extending radially outward from body portion 82 in the outwardly extending directions of lobes 110, 114. First and second pins 228, 232 can extend from flange 220 toward distal end 54, as shown in FIG. 9. In the exemplary configuration illustrated, first and second pins 228, 232 can extend from respective first and second ends 236, 240 of flange 220 and can be configured to be received in respective holes 244, 248 in bone plate 18, as will be discussed in greater detail below.

Each pin 228, 232 can include a first end 252 fixed to flange 220 and a second opposite end 256 having a taper or lead-in chamfer 260 configured to facilitate ease of entry of pins 228, 232 into holes 244, 248. In one exemplary configuration, first pin 228 can include a solid construction and/or uninterrupted outer surface having an outer diameter sized and shaped for a slip-fit into first hole 244. The second pin 232 can include a hollow construction with a slot or channel 264 extending from the second end 256 at least partially toward the first end 252, as shown in FIG. 9. Second pin 232 can include an outer diameter larger than an inner diameter of second hole 248 so as to be received therein in a press-fit manner. In this regard, the hollow and slotted construction of second pin 232 can provide for pin 232 having an elastic radial compliance when press-fit into second hole 248 and then removed therefrom.

In the exemplary configuration illustrated, the first pin 228 can, among other things, serve as a locator and the second pin 232 can serve as a locator and/or a retainer in connection with respective first and second holes 244, 248. In this regard, drill guide 14, when coupled to bone plate 18, can be used to hold and/or manipulate a position of bone plate 18 via the quick-connect arrangement 70B and the press-fit nature of pin 232.

In operation, drill guide 14 can be removably coupled to bone plate 18 such that lobes 110, 114 engage cut-outs 170, 174 in a similar manner to that discussed above. In addition, first and second pins 228, 232 can be received in respective first and second holes 244, 248 as drill guide 14 is advanced into bone plate 18 until flange 220 engages top surface 208, as shown in FIGS. 10 and 11. Flange 220 and pins 228, 232 can provide additional stability and alignment support of drill guide 14 relative to bone plate 18 and the axis of hole 26. In addition, second pin 232 can provide a retention feature to aid in retaining drill guide 14 relative to bone plate 18 until guide 14 is removed therefrom by the surgeon.

With additional reference to FIGS. 12-17, another exemplary quick-connect arrangement 70C associated with the distal end 54 of drill guide 14 is shown in accordance with the present teachings. Quick-connect arrangement 70C can be similar in certain aspects to quick-connect arrangements 70, 70A and 70B such that like reference numbers refer to like or corresponding features and only differences will be discussed in detail below. With initial reference to FIG. 12, quick-connect arrangement 70C can include flange 220 with a pair of pins 280 extending therefrom in place of first and second pins 228, 232. Each pin 280 can include a t-shaped configuration 284 formed from a first portion or member 288 extending from flange 220 and a second portion or member 292 fixed to first member 288. The second member 292 can have a larger diameter than the first member 288 and can cooperate with a coupling arrangement 296 in bone plate 18 to removably retain drill guide 14 thereto, as will be discussed in greater detail below. First and second members 288, 292 can be separate members fixed together or an integrally formed unitary member. The tapered end 86 of bone plate engaging portion 66 does not include the lobes 110, 114 in this exemplary configuration, as shown for example in FIG. 12.

Figure 13:
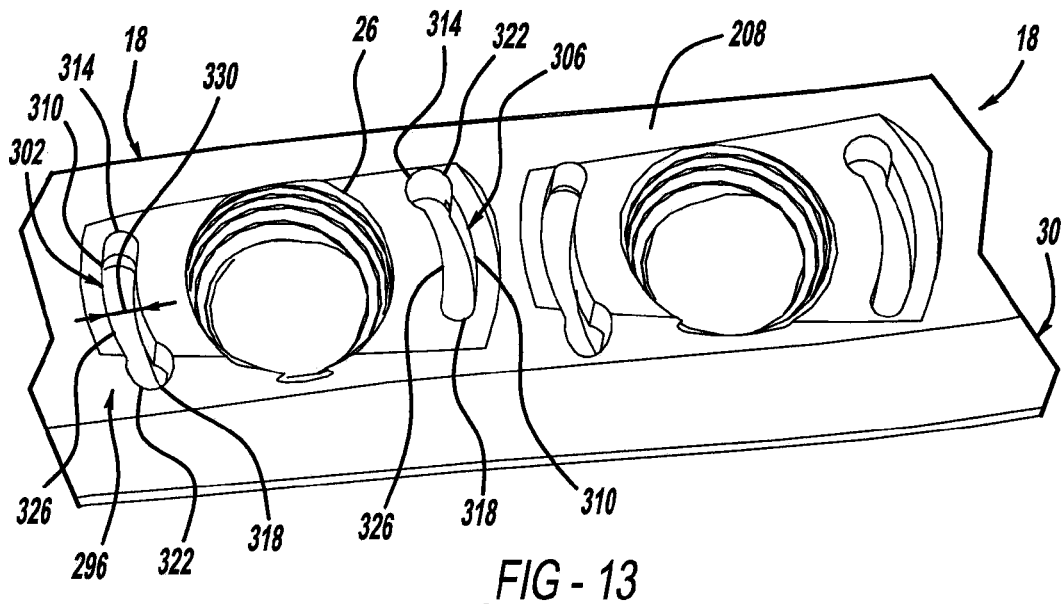
FIG. 13 is a partial perspective view of an exemplary coupling aspect of an exemplary bone plate in accordance with the teachings of the present disclosure.
Figure 14:
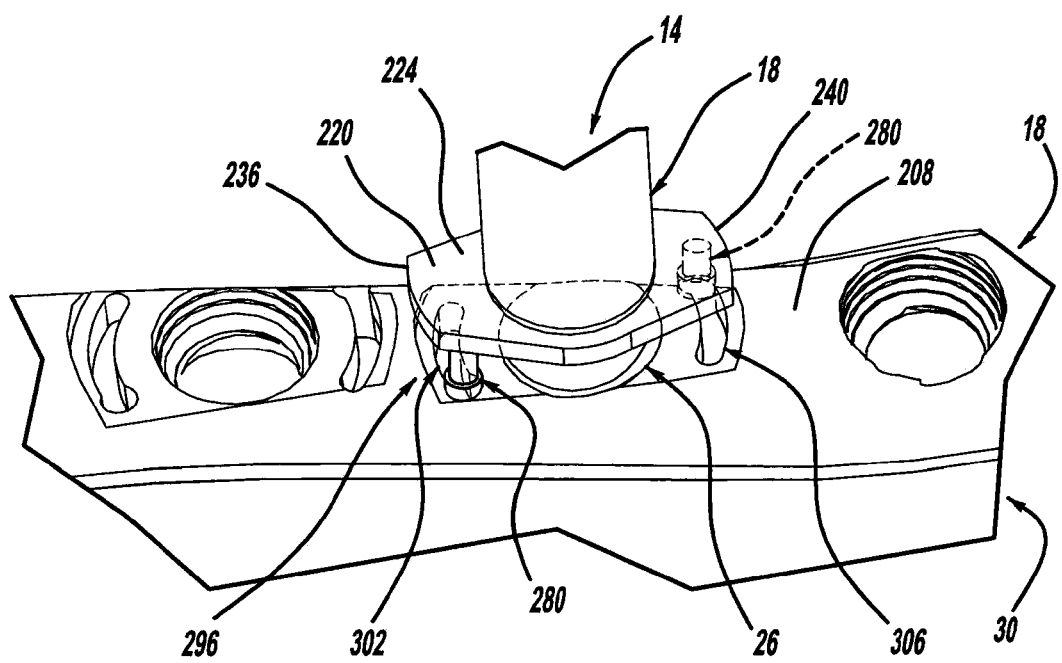
FIGS. 14-17 are views illustrating the drill guide of FIG. 12 being releasably coupled to the bone plate of FIG. 13 in accordance with the teachings of the present disclosure.
Figure 15:
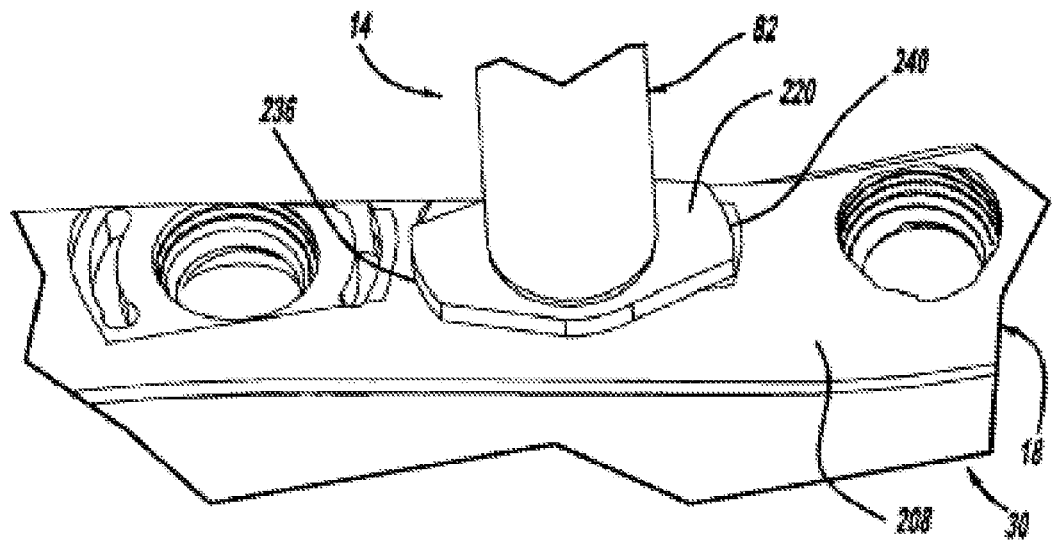
Figure 16:
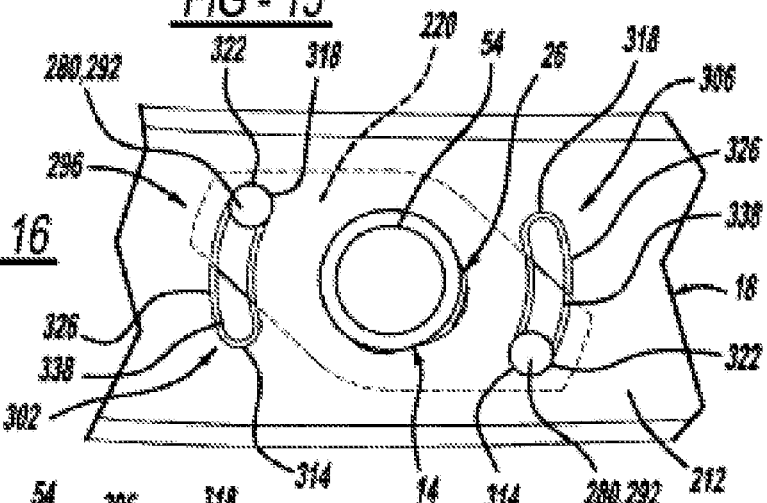
Figure 17:
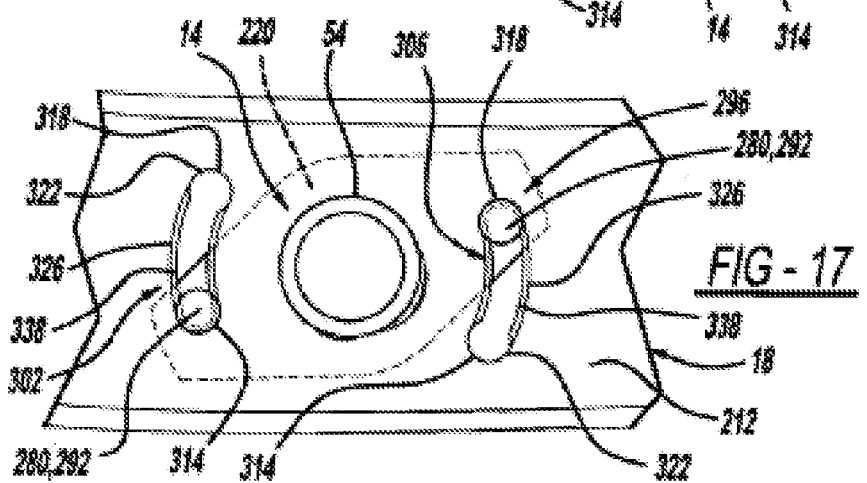

With additional reference to FIGS. 13 and 16-17, the coupling arrangement 296 of bone plate 18 can include first and second slots 302, 306 formed therein relative to hole 26 so as to align with pins 280 when the distal end 54 of drill guide 14 is advanced into bone plate hole 26. It should be appreciated that while bone plate hole 26 is shown in FIGS. 13-17 without cut-outs 170, 174, quick-connect arrangement 70C could also be utilized with bone plate hole 26 having cut-outs 170, 174. In the exemplary configuration illustrated in FIG. 13, the first and second slots 302, 306 can be positioned about longitudinal sides of hole 26. The first and second slots 302, 306 can each include an arcuate shape 310 extending between first and second ends 314, 318 so as to facilitate rotatable receipt of pins 280, as will be discussed in greater detail below. In this regard, the first slot 302 can include an enlarged opening 322 at one of the first and second ends 314, 318 and the second slot 306 can include the enlarged opening 322 at the other of the first and second ends 314, 318.

In the exemplary configuration illustrated in FIG. 13, the enlarged openings 322 can be positioned at the second end 318 of first slot 302 and at the first end 314 of the second slot 306 and can be sized and shaped to receive the second portion 292 of pins 280 therethrough. A remaining portion 326 of slots 302, 306 between the enlarged openings 322 and the other respective opposite ends can include a width 330 larger than a width 334 of the first portion 288 of pins 280, but smaller than a width 336 of second portion 292 so as to retain pins 280 in slots 302, 306 when the drill guide 14 is rotated relative thereto, as will be discussed in greater detail below.

With particular reference to FIG. 16, the first and second slots 302, 306 can include an undercut or recess 338 formed in the remaining portions 326 relative to the bone engaging side 212. The undercuts 338 can be configured to receive the second portions 292 of pins 280 when the pins are rotated from the enlarged opening 322, as will be discussed in greater detail below. In one exemplary configuration, a distance from the top surface 208 of bone plate 18 to the undercuts 338 can be substantially equal to or slightly less than a distance 342 (FIG. 12) from the flange 220 to the second portion 292 of pins 280. In another exemplary configuration, the undercuts 338 can be angled or ramped such that the distance between the top surface and each undercut 338 increases as each undercut extends from the enlarged opening 322 to the respective opposite end. The increased distance or thickness at the respective opposite ends of each undercut 338 can be greater than the distance 342 thereby creating a wedge or interference fit when pins 280 are rotated from the enlarged opening 322 to the respective opposite ends of slots 302, 306.

In operation, drill guide 14 can be advanced toward bone plate 18 such that the distal end 54 approaches bone plate hole 26. In advancing drill guide 14 toward bone plate hole 26, drill guide 14 can be positioned so as to align pins 280 with the enlarged openings 322 of slots 302, 306, as shown for example in FIG. 14. Drill guide 14 can be advanced toward bone plate 18 such that the second portion 292 of pins 280 extend through the enlarged openings 322 and the tapered end 86 is received in bone plate hole 26, as shown for example in FIG. 15. At this point, flange 220 can be in contact or engagement with top surface 208 of bone plate 18, as also shown in FIG. 15.

Drill guide 14 can then be rotated relative to bone plate 18 about hole axis 24 so as to rotate pins 280 from the enlarged openings 322 shown in FIG. 16 to the respective opposite ends of slots 302, 306, as shown in FIG. 17. In the exemplary configuration illustrated in FIGS. 12-17, drill guide 14 can be rotated clockwise approximately 45 degrees to move pins 280 from the enlarged openings to the respective opposite ends of slots 302, 306. As pins 280 move from the enlarged openings 322, the first portions 288 are received in slot portions 326 such that the second portions 292 engage the respective undercuts 338 thereby retaining drill guide 14 removably secured to bone plate 18. In this configuration, drill guide 14 can also be used to hold, retain and/or manipulate a position of bone plate 18.

In the exemplary configuration where the surfaces of the undercut are inclined or ramped in the manner discussed above, the pin second portions 292 can wedge against the respective undercuts 338 to aid in retaining drill guide 14 in the rotated position shown in FIG. 17. To remove drill guide 14 from bone plate 18, the surgeon or user simply rotates guide 14 in the opposite direction (e.g., counterclockwise) to align pins 280 with enlarged openings 322. Drill guide 14 can then be slidably retracted from bone plate 18.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A drill guide assembly, comprising:
  a. a bone plate having a bone-engaging surface, a top surface opposite to the bone-engaging surface, a bone screw hole extending through the top and bone-engaging surfaces of the bone plate adapted to receive a bone screw, and first and second apertures formed in the bone plate about opposed lateral sides of the bone screw hole, the bone screw hole including:
    a threaded portion; and
    a drill guide-engaging portion, the drill guide-engaging portion disposed between the threaded portion and the bone-engaging surface of the bone plate, the drill guide engaging portion including first and second cut-outs formed in a sidewall of the bone screw hole; and
  b. a drill guide including:
    a body having a proximal end and a distal end, the distal end having a bone plate-engaging portion;
    first and second lobes projecting radially outward from an outer surface of the bone plate engaging portion;
    an internal guide passage extending through the body between the proximal and distal ends of the body;
    a flange extending radially outward from the body configured to engage the top surface of the bone plate, the flange including a first end spaced apart from a first side of the body in a direction of the first lobe and a second end spaced apart from a second opposite side of the body in a direction of the second lobe; and
    first and second pins extending from the respective first and second ends of the flange axially alongside the distal end of the body;
    wherein the plate-engaging portion of the drill guide is configured to be slidably received in the bone screw hole of the bone plate such that the first and second lobes are received in the respective first and second cut-outs, and the first and second pins are received in the first and second apertures to removably couple the drill guide to the bone plate to allow drilling a hole in a bone through the internal guide passage in alignment with the bone screw hole.

2. The drill guide assembly of claim 1, wherein the first and second lobes each comprise arcuate outer surfaces extending only partially circumferentially around the bone plate-engaging portion so as to form an oblong shaped distal end in cross section, the first and second lobes adapted to be received in correspondingly sized and shaped cut-outs formed in a sidewall of the bone screw hole.

3. The drill guide assembly of claim 2, wherein the arcuate outer surface of each of the first and second lobes is hemispherical.

4. The drill guide assembly of claim 2, wherein the outer surface of the bone plate-engaging portion includes a tapered sidewall having an axially extending arcuate outer surface.

5. The drill guide assembly of claim 4, wherein the first and second lobes are diametrically opposed from each other.

6. The drill guide assembly of Maim 4, wherein each of the first and second lobes extend up to 90 degrees circumferentially around the bone-engaging portion of the body.

7. The drill guide assembly of claim 1, wherein the first and second lobes project radially outward from the outer surface of the bone plate-engaging portion in opposite directions from each other.

8. The drill guide of claim 1, wherein the second pin comprises an axially extending slot formed therein and a larger width than a width of the second aperture such that the second pin is removably received in the second aperture in a press-fit manner.

9. A drill guide assembly, comprising:
  a. a drill guide including:
    a body having a proximal end and a distal end, the distal end having a bone plate engaging portion;
    at least one lobe projecting radially outward from an outer surface of the bone plate-engaging portion, such that the distal end of the body has a first distal end diameter, measured at a first portion of the distal end of the body including the at least one lobe, that is greater than a second distal end diameter, measured at a second portion of the distal end of the body which does not include the at least one lobe;
    an internal guide passage extending through the body between the proximal and distal ends of the body;
    a flange extending outward from the body configured to engage the top surface of the bone plate, the flange including at least one radial end extending away from the body in a direction of the at least one lobe; and
    at least one pin extending from the flange axially alongside the distal end of the body; and
  b. a bone plate having a bone-engaging side, an top surface opposite to the bone-engaging surface, a bone screw hole extending through the top and bone-engaging surfaces of the bone plate adapted to receive a bone screw, and at least one aperture formed in the bone plate at a lateral side of the bone screw hole, the bone screw hole including:
    a threaded portion; and
    a drill guide-engaging portion, the drill guide-engaging portion disposed between the threaded portion and the bone-engaging side of the bone plate, the drill guide-engaging portion having at least one cut-out formed in a sidewall of the bone screw hole that is sized and shaped to correspond to the at least one lobe;
    wherein the plate-engaging portion of the drill guide is configured to be slidably received in the bone screw hole of the bone plate such that the at least one lobe is received in the at least one cut-out, and the at least one pin is received in the at least one aperture to removably couple the drill guide to the bone plate to allow drilling a hole in a bone through the internal guide passage in alignment with the bone screw hole.

10. The drill guide assembly of claim 9, wherein the at least one lobe comprises first and second lobes, and the at least one cut-out comprises first and second cut-outs.

11. The drill guide assembly of claim 10, wherein the first and second lobes are diametrically opposed from each other and each include an arcuate outer surface extending only partially circumferentially around the bone plate-engaging portion so as to from a generally oblong shape at the distal end, the arcuate outer surfaces configured to engage a sidewall of the respective first and second cut-outs.

12. The drill guide assembly of claim 11, wherein the arcuate outer surfaces of the first and second lobes are hemispherical.

13. The drill guide assembly of claim 10, wherein each of the first and second lobes extends up to 90 degrees circumferentially around the bone plate-engaging portion of the body.

14. The drill guide assembly of claim 10, wherein the first and second cut-outs extend in opposite directions along a longitudinal axis of the bone plate.

15. A drill guide assembly, comprising:
a. a bone plate having a bone-engaging surface, an top surface opposite to the bone-engaging surface, a bone screw hole extending through the top and bone-engaging surfaces of the bone plate adapted to receive a bone screw, and first and second apertures formed in the bone plate about opposed lateral sides of the bone screw hole, the bone screw hole including:
 a bone screw-engaging threaded portion; and
 a drill guide-engaging portion, the drill guide-engaging portion disposed between the bone screw-engaging threaded portion and the bone-engaging surface of the bone plate, the drill guide-engaging portion including at least one cut-out formed in a sidewall of the bone screw hole; and b. a drill guide including:
 a body having a proximal end and a distal end, the distal end having a bone plate-engaging portion;
 at least one lobe projecting radially outward from an outer surface of the bone plate engaging portion;
 an internal guide passage extending through the body between the proximal and distal ends of the body;
 a flange extending radially outward from the body configured to engage the top surface of the bone plate, the flange including a first end spaced apart from a first side of the body in a direction of the at least one lobe and a second end spaced apart from a second opposite side of the body; and
 first and second pins extending from the respective first and second ends of the flange axially alongside the distal end of the body;
wherein the plate-engaging portion of the drill guide is configured to be slidably received in the bone screw hole of the bone plate such that the at least one lobe is received in the at least one cut-out, and the first and second pins are received in the first and second apertures to removably couple the drill guide to the bone plate to allow drilling a hole in a bone through the internal guide passage in alignment with the bone screw hole.

* * * * *

UNITED STATES PATENT AND TRADEMARK OFFICE
CERTIFICATE OF CORRECTION

PATENT NO. : 9,867,627 B2  
APPLICATION NO. : 14/950105  
DATED : January 16, 2018  
INVENTOR(S) : Fritzinger et al.

Page 1 of 1

It is certified that error appears in the above-identified patent and that said Letters Patent is hereby corrected as shown below:

In the Claims

In Column 10, Line 1, in Claim 6, delete "Maim 4," and insert --claim 4,-- therefor In Column 10, Line 35, in Claim 9, delete "an" and insert --a-- therefor In Column 10, Line 65, in Claim 11, delete "from" and insert --form-- therefor In Column 11, Line 12, in Claim 15, delete "an" and insert --a-- therefor Signed and Sealed this  
Eighteenth Day of June, 2019

Andrei Iancu  
*Director of the United States Patent and Trademark Office*